United States Patent [19]

Kurose et al.

[11] 4,196,297

[45] Apr. 1, 1980

[54] PROCESSES FOR SEPARATING OF ENANTIOMERS BY CRYSTALLIZATION

[75] Inventors: Nancy S. Kurose, Norwalk; Arnold Zweig, Westport, both of Conn.

[73] Assignee: American Cyanamid Company, Stamford, Conn.

[21] Appl. No.: 958,219

[22] Filed: Nov. 6, 1978

[51] Int. Cl.² .......................................... C07D 233/32
[52] U.S. Cl. ................................................... 548/320
[58] Field of Search ........................................ 548/320

[56] References Cited

PUBLICATIONS

Conant et al., The Chemistry of Organic Compounds 4th ed. 255–257 N.Y., MacMillan Co., 1952.

*Primary Examiner*—Natalie Trousoe
*Attorney, Agent, or Firm*—Harry H. Kline

[57] ABSTRACT

Processes for the separation of enantiomers, such as those of 1-(2-methoxyethyl)-4-phenyl-2-imidazolidone, which comprises crystallizing a racemic mixture from a solution of the enriched enantiomer in a selective solvent.

8 Claims, No Drawings

PROCESSES FOR SEPARATING OF ENANTIOMERS BY CRYSTALLIZATION

BACKGROUND OF THE INVENTION

The present invention relates to novel processes for obtaining purified enantiomers of optically active compounds, and more particularly, it relates to processes for separating the preponderant optical isomer from mixtures containing the d,l racemate of compounds such as 1-(2-methoxyethyl)-4-phenyl-2-imidazolidone.

Organic compounds containing one or more asymmetric carbon atoms are capable of existing in the form of optical isomers, or enantiomers. Such isomers cannot readily be separated from each other by ordinary chemical means, since many of their properties, both physical and chemical, are identical or substantially identical. However, in many biological uses, one of the isomers will possess a desired activity, while the other possesses little or no activity or can even have undesirable effects. Thus, it becomes very important in certain instances to be able specifically to provide one of the two isomers.

Such optical activity effects are found in the preparation and use of tetramisole, which is a d,l mixture of two enantiomers. The S—(—)— form of tetramisole, also known as "levamisole" and shown in U.S. Pat. No. 3,463,786, is very active as an anthelmintic, while the R—(+)—isomer, also known as "dexamisole", does not have these desirable anthelmintic properties.

Historically, the first technique for the resolution, or separation, of racemic mixtures of two optical isomers into single isomers was the physical separation of crystals of the two optical isomers of tartaric acid salt by Pasteur. This technique requires that the two isomers have different crystal forms, and this difference in appearance occurs in relatively few materials. It is accordingly usually necessary to separate the isomers by some other technique. Such techniques can be costly, time-consuming, and inefficient.

These other methods for resolving racemic mixtures involve such expedients as reacting a racemate with a particular optically active material which preferentially selects one enantiomer or by a biological process wherein a micro-organism produces one enantiomer, or feeds on one enantiomer and leaves the other which can then be recovered. Unfortunately, there are not always micro-organisms which consume or produce a particular enantiomer. The chemical separation methods require particular reagents and numerous steps, first to react the racemix mixture to form a compound and then to recover the desired enantiomer from the compound after resolution.

THE INVENTION

It has surprisingly been found according to the present invention that certain enriched racemic mixtures can be separated by dissolving them in selected solvents and crystallizing material from the solvents by cooling to leave one enantiomer in solution. Briefly, the present invention affords processes for recovering enantiomers, which processes comprise dissolving racemic materials enriched in the l-isomer such as 1-(2-methoxyethyl)-4-phenyl-2-imidazolidone in certain solvents, cooling the solvent to precipitate racemic material, separating the crystals from the solvent, and recovering a purified enantiomer from the solvent. It has also been found possible in certain embodiments actually to produce crystals which can be mechanically separated or classified to produce very pure enantiomers.

The material of predominant interest for the optical resolution processes of the present invention is 1-(2-methoxyethyl)-4-phenyl-2-imidazolidone (I), having the formula

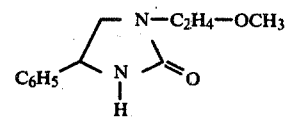

The present process is applied to compositions which are enriched in one of the two possible enantiomers, but which contain substantial amounts of the other enantiomer.

The quantity of excess material in the form of one or the other enantiomer can vary. Generally, depending upon the further use of the product, there is little need to separate the enantiomers if one of them comprises as little as five percent of the mixture. On the other hand, the processes of the present invention will operate to separate materials having any degree of enrichment. However, in general commercial practice, it is preferable that the mixture contain 60 percent or more of one of the two enantiomers. Herein, compositions containing substantial quantities of both enantiomers with an excess of one enantiomer will be denominated "enriched" mixtures.

One source of imidazolidone (I) is the acylate of 1-(2-methoxyethyl)-4-phenyl-4-imidazolin-2-one which has been hydrogenated with a rhodium complex catalyst and then hydrolyzed to provide the free (I). Such rhodium catalysts can be tailored to favor one or the other configuration at the prochiral C-4 atom, and the fully saturated ring obtained is chiefly in the form of one enantiomer, but the other enantiomer can be present as well.

An important utility of the purified enantiomer produced according to the invention is as an intermediate for further chemical processes. Thus, the S-enantiomer can be treated with phosphorus pentasulfide to provide levamisole, a base used to make products having excellent anthelmintic properties as stated in the aforementioned U.S. Pat. No. 3,463,786. The R-enantiomer can similarly be treated with phosphorus pentasulfide to provide dexamisole. The particular chirality of these materials is quite important in pharmaceutical and veterinary uses.

The resolution according to the present invention is effected through use of certain selective solvent systems. The enriched racemic mixture is dissolved in a suitable solvent as taught herein. After the mixture is totally in solution, the temperature of the solvent is then lowered to provide crystallization and consequent precipitation of the resulting crystals. To effect dissolution of the enriched racemate, the solvent can be warmed if necessary. If impurities are present so that all of the solids do not dissolve, the undissolved solids can be removed from the liquid by conventional techniques, such as settling, filtration, centrifugation, and the like.

The selective solvent systems used in the present invention are certain lower glycol ethers and mixtures of ethers or hydrocarbons and alkyl esters. The desirable selective solvents used herein are alkylene glycol dialkyl ethers, and mixtures of mobile liquid aliphatic ethers or saturated hydrocarbons with esters of aliphatic alcohols and aliphatic carboxylic acids. The selective solvents used herein are liquids at the temperatures used for dissolving the racemate and are sufficiently mobile at the dissolution and crystallization temperatures that the crystals formed move relatively freely through the liquid.

The glycol ethers can be used singly or in admixture. The alkylene group is desirably a lower alkylene group and preferably contains from two to four carbon atoms, while the ether groups substituent thereon contain from one to about four carbon atoms. A particularly preferred glycol ether used in the practice of the present invention is ethylene glycol diethyl ether.

The ethers used in admixture with the esters described herein are lower alkyl ethers having the same or different alkyl groups substituent on the ether oxygen. Preferred ether groups contain from three to six carbon atoms, and diethyl ether is especially preferred in certain embodiments of the invention.

The hydrocarbons used in admixture with esters to provide selective solvents are desirably lower aliphatic and cycloaliphatic hydrocarbons, including both straight and branched-chain isomers, having from four to about ten carbon atoms in the molecule. Very short chain hydrocarbons are more volatile than the longer chain materials, and so require the use of lower temperatures and/or superatmospheric pressures, as described herein. The cycloaliphatic hydrocarbons contemplated by the present invention are those having the same mobility and volatility characteristics as the aliphatic materials. Such cycloaliphatics can also be alkyl-substituted, and desirably contain from six to ten carbon atoms. For reasons of cost, availability, and properties providing good selectivity, cyclohexane is a preferred cycloaliphatic component.

A variety of commercial aliphatic hydrocarbons are available. These can be obtained with a variety of boiling ranges. One particularly preferred aliphatic hydrocarbon component of the present invention is "hexanes", which is actually a mixture of normal and isomeric hexanes; such commercial mixtures used herein can also contain quantities of hydrocarbons having different chain lengths, but sharing similar volatility and mobility.

The esters used as components in the selective solvents are likewise selected with mobility, polarity, and volatility as criteria. Generally, the ester components are the esters of aliphatic acids containing from two to six carbon atoms and aliphatic alcohols containing from two to six carbon atoms. While a wide range of esters can be utilized, it is preferable that the total number of carbon atoms in the esters be from about four to about six. For reasons of availability, economy, and the surprisingly good separation afforded according to the present processes, ethyl acetate is a preferred ester.

The two-component selective solvents used herein can comprise from about two parts by volume to about 15 parts by volume of the hydrocarbon or ether component for each part by volume of ester component. The precise amounts of the two components can be varied within the stated range to obtain the desired separation and the desired physical properties of mobility, polarity, volatility, and the like. In preferred embodiments of the invention, the quantity of non-ester component is from about two to about ten times the volume of the ester component.

Solubility characteristics also play a part in determining the parameters of the process. It is generally desired that one kilogram of the racemate be dissolved in from five to 30 liters of the solvent. Dilutions in this range provide reasonable celerity of solution with good crystal formation.

The temperatures used in the present processes can vary over a range. The particular selective solvent used will to some extent govern the desired temperatures. The upper temperature is chosen to provide good solution of the enriched racemate, and the lower temperature is chosen to provide the desired crystallization. Dissolution of the enriched racemate is desirably carried out at temperatures of from about 15° to about 70° C., and crystallization is carried out at any temperature at which crystals form, down to temperatures where the solvent freezes or becomes too viscous or difficult to handle. Crystallizations are generally carried out at temperatures from 45° C. down to −40° C. It is preferred that crystallizations be carried out from room temperature, say, 21°–25° C., down to −20° C.

Dissolving the enriched racemate in the selective solvent is generally a fairly rapid procedure which consumes from 15 minutes to one hour, depending upon the quantity involved and the particular solvent system. The crystallization time desirably ranges from one hour to 24 hours, and in preferred embodiments of the invention crystallization is carried out for from two hours to about six hours.

The selective solvent can be used at subatmospheric or superatmospheric pressures, and in most instances there is little advantage to the use of subatmospheric pressure. Superatmospheric pressures up to perhaps two atmospheres can be used when the selective solvent is volatile. However, in many of the most advantageous embodiments, the processes of the present invention are carried out at atmospheric pressure.

After the crystals have formed, they can be separated from the supernatant liquid by conventional processes. These include settling, filtration, centrifugation, and the like. The crystals so separated are generally close to being a racemic mixture, and it is in fact desirable that the optical rotation of the crystallized material be as small as possible, since this indicates a good separation.

While other methods of ascertaining the separation can be employed, it is useful herein to observe the specific optical rotation for purposes of determining purities of the racemate, the separated crystals, and the final product. These are determined and recorded as $[\alpha]_D^{20}$ in an appropriate solvent. Chloroform is generally used herein as the solvent for purposes of determining specific optical rotation.

After separation of the crystals from the supernatant liquid, the selective solvent is removed from the remaining solute by conventional means, such as evaporation, vacuum evaporation, and the like. In some instances it may be useful to heat the supernatant liquid separated from the crystals to shorten the evaporation time. One of the advantages of the present invention is that the solvent can be recovered from the evaporation step and recycled for further use in the process.

It has also surprisingly been found that advantages accrue through use of a second treatment of the recovered solute with the solvent. Thus, in certain preferred embodiments the purified enantiomer obtained after evaporation of the selective solvent is redissolved in smaller quantities of hot selective solvent, that is, at temperatures up to the boiling point of the selective solvent, and then let stand until room temperature (25° C.) is reached. This procedure causes the formation of two different types of crystals, one being fine crystals of racemate which tend to remain suspended and settle more slowly, and the other being larger, heavier crystals of the S-enantiomer which settle more rapidly. These two types of crystals can be separated from the solvent by mechanical means, such as a classifier, a wet cyclone, or the like.

It is found that the fine crystals which do not settle as readily are a substantially pure racemic mixture while large crystals are substantially pure S-enantiomers. Further recrystallization of the dense crystals is carried out with the same selective solvents and in the same manner as the original crystallization. It will be appreciated that such a recrystallization is one preferred embodiment which confers even greater advantages to the processes disclosed herein.

The following Examples are given to illustrate embodiments of the invention as it is presently preferred to practice it. It will be understood that these Examples are illustrative, and the invention is not to be considered restricted thereto except as indicated in the appended Claims.

EXAMPLE I

A 1.0 g sample of enriched racemic 1-(2-methoxyethyl)-4-phenyl-2-imidazolidone having an optical rotation, $[\alpha]_D^{20}$, in chloroform, of $-17.4°$ is added to 4 cc of ethylene glycol dimethylether and gently heated so that all of the solid material goes in the solution. After complete dissolution of the solid, the solution is chilled to $-20°$ C. and held for approximately three hours.

After the three-hour interval, the crystals which have formed in the solution are separated by filtration. The solvent is removed from the remaining solution by vacuum evaporation. The 0.23 g of solids obtained by filtration has an optical rotation of $-2.2°$, and the approximately 0.77 g from the solution is found to have an optical rotation of $-22.8°$.

It is thus apparent that the precipitate is a racemic mixture and the material remaining in the solution is levorotatory. A very substantial proportion of the levorotatory R—(—) enantiomer is thereby obtained in much purified optically active form.

In all succeeding Examples, the optical rotation is the $[\alpha]_D^{20}$ in chloroform.

EXAMPLE II

The procedure of Example I is repeated by dissolving a 1 g sample of the same imidazolidone in 22 cc of a 10:1 V/V diethylether: ethylacetate selective solvent and chilling the solution to 0° C. for one hour and then to $-20°$ C. for an additional two hours. The crystals precipitated from the solution weight 0.39 g and have an optical rotation of $-2.1°$. After drying, the material recovered from the solute weights 0.52 g and has an optical rotation of $-28.3°$.

EXAMPLE III

A 1 g sample of 1-(2-methoxyethyl)-4-phenyl-2-imidazolidone having an optical rotation of $+17.7°$ is dissolved in 22 ml of a 10:1 diethylether: ethylacetate solution. After dissolution is complete, the resulting solution is held at $-20°$ C. for three hours. The precipitate crystals having an optical rotation of $+2.0°$ weigh 0.368 g and the material obtained after evaporation of the solvent has an optical rotation of $+27.4°$ and weighs 0.602 g.

EXAMPLES IV–IX

The procedure of Example III is repeated with the same amount of the same imidazolidone, utilizing different solvents and/or temperatures. The results are shown in Table I, wherein the crystallization temperature is room temperature, that is, about 21° C., and "EtOAc" is ethyl acetate.

| Example | Solvent | Ratio (v/v) | Solvent Volume (ml) | Crystallization Time (hrs) | Precipitate wt. | Precipitate α | Residue wt. | Residue α |
|---|---|---|---|---|---|---|---|---|
| IV | Hexanes:EtOAc | 2.5:1 | 10 | 5 hrs. | 0.396 | +4.9 | 0.577 | +27.4 |
| V | Cyclohexane:EtOAc | 10:1 | 20 | 5 hrs. | 0.470 | +7.7 | ~0.5 | +27.4 |
| VI | Hexanes:EtOAc | 2.5:1 | 15 | 3 hrs. | 0.351 | +3.1 | 0.629 | +26.7 |
| VII | Cyclohexane:EtOAc | 5:1 | 15 | 3 hrs. | 0.346 | +3.6 | 0.626 | +26.0 |
| VIII | Cyclohexane:EtOAc | 3:1 | 10 | 3 hrs. | 0.315 | +2.8 | 0.676 | +25.2 |
| IX | Hexanes:EtOAc | 2.5:1 | 12 | 3 hrs. | 0.376 | +3.9 | 0.592 | +27.4 |

EXAMPLE X

A 1 g sample of 1-(2-methoxyethyl)-4-phenyl-2-imidazolidone having an optical rotation of $+17.3°$ is dissolved in 2.5:1 hexanes:ethylacetate. The solution is held at 45° C. for one hour and then overnight (approximately 16 hours) at a room temperature of about 21° C. The precipitate weighing 0.348 g has an optical rotation of $+1.8°$, while the 0.624 g recovered from the solution after removal of the solvent has an optical rotation of $+27.3°$. It will be appreciated from these data that the low optical activity of the precipitate crystals indicates a very good separation has taken place.

EXAMPLES XI–XIII

A series of tests is run utilizing the indicated amounts of a 1-(2-methoxyethyl)-4-phenyl-2-imidazolidone having an optical rotation of $-16.4°$. The results are set forth in Table II, where "RT" indicates room temperature.

TABLE II

| Example | Mixture Amount | Solvent | Ratio (v/v) | Solvent Volume (ml) | Crystallization Temp. | Crystallization Time | Precipitate wt. | Precipitate α | Residue wt. | Residue α |
|---|---|---|---|---|---|---|---|---|---|---|
| XI | 0.3 g | Ether:EtOAc | 10:1 | 11 | −20° C. | ~3 hrs. | 0.1 | −1.4 | 0.2 | −23.4 |
| XII | 0.5 g | Ether:EtOAc | 10:1 | 11 | −20° C. | 1 day | 0.171 | — | 0.286 | −24.5 |
| XIII | 1.0 g | Hexanes:EtOAc | 2:1 | 10 | RT | 3 days | 0.291 | −3.3 | 0.568 | −24.9 |

EXAMPLE XIV

A rhodium complex catalyst is used to hydrogenate the acylate of 1-(2-methoxyethyl)-4-phenyl-4-imidazolin-2-one to provide after hydrolysis 15.7 g of a mixture of d,l-1-(2-methoxyethyl)-4-phenyl-2-imidazolidone containing 63% excess S-enantiomer. This product is dissolved in 190 ml of a 2.5:1 V/V mixture of hexanes:ethylacetate. The solution is cooled to room temperature to provide 4.1 g of crystalline racemate having an optical rotation of +2.9° and leaving in the solution 11.6 g of an enriched material which on isolation has an optical rotation of +25.6°.

Recrystallization of this isolated material from the same solvent system yields a product containing two distinct crystalline forms. One form is light, fine needles, and the other is dense, thick needles.

The two different crystalline forms are mechanically separated by slurrying with solvent and decantation of the supernatant liquid. This leaves dense crystals having an optical rotation of +32.2°. Recrystallization of this material provides dense crystals having an optical rotation of +32.8°. The crystals of this pure S-isomer have a melting point of 74°-75° C. These crystals are morphologically distinguished by their significantly large size which makes them mechanically separable, such as by classification.

NMR (nuclear magnetic resonance) studies demonstrate that the recrystallized dense crystals are substantially pure S-isomer. A sample of this substantially pure isomer is treated with phosphorus pentasulfide and hydrochloric acid to yield a high quality levamisole.

EXAMPLE XV

A 15.6 g sample of enriched racemic 1-(2-methoxyethyl)-4-phenyl-2-imidazolidone having $[\alpha]_D^{20}$ (C=1, CHCl$_3$) of +19.7°, equivalent to a 61.2% excess of the S-enantiomer is added to 185 cc of a 2.5:1 V/V hexanes:ethylacetate mixture and gently heated so that all of the solid material goes into solution. The solution is cooled to 45° C. and held at 40°-45° C. for three hours, during which crystals form.

The liquid is then cooled to 35° C. and held for one hour at 30°-35° C. while additional crystals form, and then it is held at 25° C. for 18 hours. The approximately 5 g of crystals formed are recovered by filtration and have $[\alpha]_D = +2.5°$ indicative of nearly pure racemic material (7.8% excess of S-enantiomer). The filtrate is concentrated to yield approximately 10.5 g of crystals with $[\alpha]_D^{20} = +27.5°$ (C=1, CHCl$_3$), equivalent to 84% excess of S-enantiomer of 1-(2-methoxyethyl)-4-phenyl-2-imidazolidone.

What is claimed is:

1. A process for separating optical isomers which comprises: dissolving a mixture containing a preponderance of one enantiomer of 1-(2-methoxyethyl)-4-phenyl-2-imidazolidone in a selected solvent, wherein said solvent is (A) a mixture of (1) at least one ester of lower aliphatic alcohol and lower aliphatic carboxylic acid and (2) liquid aliphatic or cycloaliphatic hydrocarbon or lower aliphatic ether, or (B) an alkylene glycol dialkyl ether, cooling the solvent to form crystals of a racemic mixture, and separating the racemic crystals from the solvent containing the preponderant enantiomer.

2. A process according to claim 1, wherein the solvent containing the preponderant enantiomer is removed by evaporation to provide purified enantiomer.

3. A process according to claim 2, wherein the enantiomer is further purified by redissolving it in said selective solvent, cooling the solvent to crystallize the enantiomer and remaining unremoved racemate, recovering resultant enantiomer and racemate in different crystalline forms, and physically separating the resultant crystals of enantiomer and racemate to obtain resolved enantiomer.

4. A process according to claim 1 wherein the ester contains from four to six carbon atoms.

5. A process according to claim 1 wherein the aliphatic hydrocarbon contains from four to ten carbon atoms, the cycloaliphatic hydrocarbon contains from six to ten carbon atoms, and the ether contains from three to six carbon atoms.

6. A process according to claim 1 wherein the alkylene group of the glycol ether contains from about two to four carbon atoms and the alkyl groups substituent on the oxygen atoms contain from one to four carbon atoms.

7. A process according to claim 1 wherein the ratio of hydrocarbon or ether to ester is from about two to about 15 parts by volume to each part by volume of ester.

8. A process according to claim 1 wherein the cooling is to room temperature.

* * * * *